United States Patent
Lee et al.

(10) Patent No.: US 7,205,418 B2
(45) Date of Patent: Apr. 17, 2007

(54) PROCESS FOR THE PREPARATION OF OPTICALLY ACTIVE 2-[6-(SUBSTITUTED ALKYL)-1,3-DIOXAN-4-YL]ACETIC ACID DERIVATIVES

(75) Inventors: Inhee Lee, Suwon-si (KR); Seungjoo Lee, Suwon-si (KR)

(73) Assignee: Choongwae Pharma Corporation, Seoul (KR)

( * ) Notice: Subject to any disclaimer, the term of this patent is extended or adjusted under 35 U.S.C. 154(b) by 219 days.

(21) Appl. No.: 10/500,023

(22) PCT Filed: Aug. 13, 2002

(86) PCT No.: PCT/KR02/01540

§ 371 (c)(1),
(2), (4) Date: Mar. 7, 2005

(87) PCT Pub. No.: WO03/053950

PCT Pub. Date: Jul. 3, 2003

(65) Prior Publication Data

US 2005/0148784 A1    Jul. 7, 2005

(30) Foreign Application Priority Data

Dec. 20, 2001   (KR) ................................. 2001-81659

(51) Int. Cl.
    *C07D 319/06* (2006.01)
(52) U.S. Cl. ...................................................... 549/375
(58) Field of Classification Search ................. 549/375
    See application file for complete search history.

(56) References Cited

U.S. PATENT DOCUMENTS 5,155,251 A * 10/1992 Butler et al. ................ 558/442
5,278,313 A *  1/1994 Thottathil et al. .......... 548/252

* cited by examiner

*Primary Examiner*—Taofiq Solola
(74) *Attorney, Agent, or Firm*—Blakely, Sokoloff, Taylor & Zafman; Stephen M. De Klerk (57) ABSTRACT

The present invention relates to new process for preparing as a key chiral intermediate compound of formula (I) obtained from an epoxy-β-hydroxy carboxylic acid ester of formula (II) prepared from epoxide compound of formula (III), in which said compound of formula (I) is useful for preparing the therapeutic agent for hyperlipidemia, such as Astrovastatin and Fluvastatin. Wherein $R_1$ denotes a hydrogen atom, alkyl, aryl or alkylaryl, $R_2$ and $R_3$ which can be identical or different, are a lower alkyl or phenyl and are capable of forming a six-membered ring, $R_4$ stands for hydroxy, amino, alkylamino, azido, cyano, halogeno, aryloxy, alkyloxy, arylalkyloxy, alkyl, alkenyl, aryl, or aminomethyl, etc.

11 Claims, 1 Drawing Sheet

FIG. 1

PROCESS FOR THE PREPARATION OF OPTICALLY ACTIVE 2-[6-(SUBSTITUTED ALKYL)-1,3-DIOXAN-4-YL]ACETIC ACID DERIVATIVES

CROSS-REFERENCE TO OTHER APPLICATIONS

This Application is a National Phase of International Application No. PCT/KR02/01540, filed on Aug. 13, 2002, which claims priority from Korean Patent Application No. 2001/81659, filed on Dec. 20, 2001.

TECHNICAL FIELD

The present invention relates to a process for preparing intermediates of pharmaceuticals, especially Statin-type pharmaceuticals such as Atrovastatin and Fluvastatin etc. or optically active 2-[6-(substituted alkyl)-1,3-dioxane-4-yl] acetic acid derivatives which are valuable as an intermediate of 3-hydroxy-3-methylglutaryl-coenzyme A(HMG-CoA reductase) repressor.

More specifically, the present invention relates to a new process for preparing a compound of formula (I) by reacting optically active epoxy alcohol of formula (II) prepared from an optically active epoxy compound of formula (III) with various substituents.

wherein $R_1$ denotes a hydrogen atom, alkyl, aryl or alkylaryl, preferably methyl, ethyl, isopropyl, or tert-butyl, $R_2$ and $R_3$ which can be identical or different, denote a lower alkyl or phenyl and are capable of forming a six-membered ring, $R_4$ stands for hydroxy, amino, alkylamino, arylamino, azido, cyano, halogeno, aryloxy, alkyloxy, arylalkyloxy, alkyl, alkenyl, aryl, or aminomethyl, etc.

BACKGROUND ART

The following processes for the preparation of optically active 2-[6-(substituted alkyl)-1,3-dioxane-4-yl]acetic acid derivatives represented by the above formula (I) are well known in the prior art.

(1) The process for the synthesis of optically active 2-[6-(hydroxy methyl)-1,3-dioxane-4-yl] acetic acid derivatives from 3-hydroxy-ɣ-butylollactone via 3,5-dihydroxyhexane acid ester derivatives (Japanese Laid Open Patent Publication No. (Hei)4-173767).

(2) The process for the synthesis of optically active 2-[6-(cyano methyl)-1,3-dioxane-4-yl]acetic acid derivatives from 3-hydroxy-4-bromoester (U.S. Pat. No. 5,155,251).

(3) The process for the synthesis of 3,5,6-trihydroxyhexane acid ester derivatives from 4-chloroacetic acid ester through transforming to benzyloxy derivatives, reducing and chain-extending (Japanese Laid Open Patent Publication No. (Hei)6-65226).

(4) The process for the synthesis of optically active 2-[6-(substituted alkyl)-1,3-dioxane-4-yl] acetic acid derivatives from 4-chloro-3-hudroxybutyric acid ester through chain-extending and reducing, etc. (U.S. Pat. No. 5,278, 313).

(5) The process for the synthesis of 3,5,6-trihydroxyhexane acid ester derivatives from malic acid via 2,4-dihydroxyadipic acid derivatives (Japanese Laid Open Patent Publication No. (Hei)4-69355).

However, since the aforementioned comprise the reactions under extremely low temperature such as around −80° C. (Processes 1, 2, 4 and 5) or the reaction of hydrogenation under the high pressure of 100 k/cm² (Process 3), they should need a particular device for the reaction. Further, the processes use a high-priced reagent such as LDA in a part of steps or others, and the starting materials used can hardly produce various derivatives or need other operations and thus have a problem to require a long reaction course. Conclusively, any one of the processes cannot be effective in the commercial scale.

On the other hand, Korean Laid Open Patent Publication No. 2001-30819 (corresponding to PCT/JP1999/04299) has disclosed a process for preparing 2-[6-(substituted methyl)-1,3-dioxane-4-yl] acetic acid derivatives from low-cost materials without the need of a particular device such as a device for extremely low temperature reaction. However, the process give rise to problems of the purification of the final diol-based compounds and industrialization since it includes a stage of producing optically active diol compounds by use of microbial strands as a key step. Besides the aforementioned process can hardly produce various derivatives because of employing microbial strands.

The Statin-type pharmaceuticals such as Atrovastatin and Fluvastatin include compounds with optically active 1,3-diol unit. Therefore, there is a continuing need for a low-cost and simple process for preparing compounds comprising optically active 1,3-diol unit as a chiral building block, e.g., optically active 2-[6-(substituted alkyl)-1,3-dioxane-4-yl] acetic acid derivatives.

We have endeavored to solve the above issue. As a result, we have discovered that the optically active 2-[6-(substituted alkyl)-1,3-dioxane-4-yl] acetic acid derivatives of the following formula (I) could be produced efficiently according to a scheme which had not been publicly known. In the course of the above study, we have also discovered that a new process for producing β-hydroxyepoxycarboxylic acid derivative of formula (II) as other intermediates for preparing various compounds of formula (I) can be developed.

wherein $R_1$ denotes a hydrogen atom, alkyl, aryl or alkylaryl, preferably methyl, ethyl, isopropyl, or tert-butyl, $R_2$ and $R_3$ which can be identical or different, denote a lower alkyl or phenyl and are capable of forming a six-membered ring, $R_4$ stands for hydroxy, amino, alkylamino, arylamino, azido, cyano, halogeno, aryloxy, alkyloxy, arylalkyloxy, alkyl, alkenyl, aryl, or aminomethyl, etc.

In addition, we have discovered a method for preparing various compounds of formula (I) by reacting β-hydroxyepoxycarboxylic acid derivative of formula (II) with various nucleophilic reagents.

Therefore, it is a first object of the present invention to provide a process for preparing the compound of formula (I).

It is a second object of the invention to provide a process for preparing the compound of formula (II) as the intermediate to produce the compound of formula (I).

DETAILED DESCRIPTION

In the present invention, the process for preparing the compound of formula (I) as shown in Scheme 2, characterized in that it comprises the following steps of:

(a) reacting an epoxide compound of formula (III) with vinyl magnesium bromide or vinyl magnesium chloride to produce a β-hydroxy compound of formula (IV);

(b) protecting the hydroxy group of β-hydroxy compound of formula (IV) with a alkyloxy carbonyl group by reacting the β-hydroxy compound of formula (IV) with dialkyldicarbonate such as di-tert-butyl dicarbonate to produce a compound of formula (V);

(c) cyclization-reacting the compound of formula (V) by a iodolactone forming reaction to produce a compound of formula (VI);

(d) treating the compound of formula (VI) with a weak base such as $K_2CO_3$, $Na_2CO_3$ to produce a compound of formula (II);

(e) producing a 1,3-diol compound of formula (VII) by a ring opening reaction of the compound of formula (II) with various nucleophiles in the presence of a metal catalyst and a phase transition catalyst;

(f) treating the 1,3-diol compound of formula (VII) with an acetylating agent or a ketalizing agent in the presence of an acid catalyst to transform the compound of formula (VII) into a compound of formula (VIII); and (g) if necessary, producing a compound of formula (I) by exchanging $R'_4$ group in the compound of formula (VIII).

Also, the present invention provides the process for preparing the compound of formula (II) as the intermediate as shown in Scheme 2, characterized in that it comprises the following steps of:

(a) reacting an epoxide compound of formula (III) with vinyl magnesium bromide or vinyl magnesium chloride to produce a β-hydroxy compound of formula (IV);

(b) protecting the hydroxy group of β-hydroxy compound of formula (IV) with an alkyloxy carbonyl group by reacting the β-hydroxy compound of formula (IV) with dialkyldicarbonate such as di-tert-butyl dicarbonate to produce the compound of formula (V);

(c) cyclization-reacting the compound of formula (V) to produce a compound of formula (VI); and

(d) treating the compound of formula (VI) with a weak base such as $K_2CO_3$, $Na_2CO_3$ to produce a compound of formula (II).

[Scheme 2]

wherein $R_1$ denotes a hydrogen atom, alkyl, aryl or alkylaryl, preferably methyl, ethyl, isopropyl, or tert-butyl, $R_2$ and $R_3$ which can be identical or different, denote a lower alkyl or phenyl and are capable of forming a six-membered ring, $R_4$ stands for hydroxy, amino, alkylamino, arylamino, azido, cyano, halogeno, aryloxy, alkyloxy, arylalkyloxy, alkyl, alkenyl, aryl, or aminomethyl, etc. and $R'_4$ is the same as $R_4$ or a group having the precursor form thereof.

Embodiments of the present invention are shown in the following Schemes 3 and 4.

wherein $R_1$ denotes a hydrogen atom, alkyl, aryl or alkylaryl, preferably methyl, ethyl, isopropyl, or tert-butyl.

wherein $R_1$ denotes a hydrogen atom, alkyl, aryl or alkylaryl, preferably methyl, ethyl, isopropyl, or tert-butyl, $R_2$ and $R_3$ which can be identical or different, denote a lower alkyl or phenyl and are capable of forming a six-membered ring, $R_4$ stands for hydroxy, amino, alkylamino, arylamino, azido, cyano, halogeno, aryloxy, alkyloxy, arylalkyloxy, alkyl, alkenyl, aryl, or aminomethyl, etc. and $R'_4$ is the same as $R_4$ or a group having the precursor form thereof.

The groups of alkyl, aryl and alkylaryl used in the present invention include $C_{1-12}$ alkyl, $C_{1-6}$alkyl, and $C_{6-12}$ alkylaryl respectively, but are not limited to them.

The term "precursor form" means a chemical which is intended to include, e.g., the precursor form of an aminomethyl group is a cyano group, and that of a hydroxy group is an acetoxy or benzyloxy group and vice versa.

The present invention is more specifically explained as follows.

In Steps (a) and (b) of Scheme 3, an epoxide compound of formula (III) or a β-hydroxy compound of formula (IV) is available from commercial compounds or materials produced by conventional methods described in the literatures (See Science 1997, 277, 936–938; JACS. 2000, 122, 1235–1236; TL. 1986, 27, 5791; JOC. 1988, 63, 1961–1973; Manufacturer: CHOONGWAE PHARMA CO.).

In Step (b), a β-hydroxycarboxylic ester of formula (IV) is reacted with dialkyl dicarbonate such as di-tert-butyl dicarbonate[(Boc)$_2$O] in the presence of a base and an organic solvent to produce a carbonate compound of formula (V). The base used in the reaction includes chemical reagents whereby a carbonate compound is produced from alcohol are generally used, but is not limited to them. Examples of a base which can be used in the presence of organic solvents, include metal base such as methyl lithium, n-butyl lithium, sodium hydride, or triethylamine, pyridine, diisopropylamine, isopropylethylamine, and a catalytic amount of N,N-dimethylaminopyridine. The reaction is carried out at temperature between −78° C. and 100° C., particularly at low temperature of −30° C.~0° C. in some cases of using a metal base.

In Step (c), an iodation reaction proceeds at the double bond position in the compound of formula (IV) by reacting the compound of formula (V) with IBr dissolved dichloromethane in the presence of toluene solvent at low temperature of −80° C., according to a conventional method (See JOC., 1993, 58, 3703–3711). Then, the iodo-lactonation forming reaction proceeds by the internal substitution via oxygen atom of the alkyloxy carbonyl group corresponding to a hydroxy-protecting group to produce 1,3-cis com- pound of formula (VI) and 1,3-trans compound of formula (VI-a) in the ratio of 18:1~21:1 (See the above reference).

However, in the proceeding of the reaction, the ratio of cis/trans is rendered unfavorable at the temperature of −80° C. or higher, and if the mixture is added IBr which dissolved dichloromethane, it is difficult to add IBr drop by drop because IBr is salted out at the low temperature. These problems can be solved by trifluoromethylbenzene instead of dichloromethane for dissolving IBr. Generally, the reaction temperature is appropriate between −80° C. and 0° C. Particularly, the highest ratio of cis/trans (i.e. 20/1 to 24/1) appears at temperature between −30° C. and −20° C.

Therefore, the present invention provides excellent processes without problems caused from use of low temperature in the prior arts. Further, trifluoromethylbenzene itself or mixed solvents with commercial organic solvents can be used. Particularly, examples of preferable solvents which can be used together with trifluoromethylbenzene, include toluene or benzene.

In Step (d), the ring-opening reaction of the six-membered ring and the cyclization for epoxide ring-forming reaction are proceeded concurrently under the basic condition.

However, where a compound having an acidic proton at the α-position such as the compounds of formula (VI) are reacted with basic reagent at room temperature, α,β-unsaturated epoxide of formula (II-a) is produced by the α,β-removal reaction as shown in Scheme 5 instead of the desired compound of formula (II).

[Scheme 5]

As a result of using many reagents under the various condition, it has been discovered that desired compound of formula (II) can be obtained good selectivity and improved yield by using weak base reagents such as 3 equivalents of potassium carbonate/methanol or sodium carbonate/methanol at temperature between −78° C. and 0° C., preferably between −30° C. and 0° C.

It is somewhat difficult to produce various compounds of formula (I) as required in the prior arts. However, according to the present invention, the compound of formula (I) from the compound of formula (II) produced as another intermediate can be produced. Accordingly, it is a merit of the invention that various compounds of formula (I) are conveniently produced according to reagents.

In Step (e) of Scheme 4, various substituents can be attached to the compound of formula (II) by the ring-opening reaction through using various kinds of nucleophilic reagents.

Examples of reagents which can be used to attach various substituents in said step include commercial reagents for epoxide ring-opening reaction, but are not limited to them. For instance, cyanide, halide, alkoxide and an azide compound of alkali metal, Grignard reagent, organometal compound or the like can be reacted under an organic solvent with metallic catalysts, acids and a phase transition catalysts.

Examples of metallic catalysts, include titanium isopropoxide[Ti(O$^i$Pr)$_4$], aluminium isopropoxide[Al(O$^i$Pr)$_3$], trifluoroboron diethylether[BF$_3$.OEt$_2$]. The metallics catalysts can be used in the amount of 0.1 times to 100 times in equivalents, preferably 0.5 times to 50 times in equivalents, more preferably 1 times to 10 times in equivalents based on the amount of the compound of formula (II).

Examples of phase transition catalysts, include crown ether, quaternary ammonium halide or quaternary potassium halide and can be added in the amount of 0.1 times to 100 times in equivalents, preferably 0.5 times to 50 times in equivalents, more preferably 1 times to 10 times in equivalents based on the amount of the compound of formula (II).

The reaction is carried out generally at temperature between −50° C. and 100° C., preferably between 0° C., and 50° C., more preferably between 10° C. and 30° C.

In Step (f), the compound of formula (VIII) having 1,3-dioxane ring can be obtained by protecting the 1,3-diol compound of formula (VII) with, for instance, acetone/CSA or dimethoxypropane/CSA etc.

In Step (g), the resulting compound of formula (VIII) is, if necessary, transformed to various derivatives by exchanging the group of R'$_4$. For example, when R'$_4$ is a cyano compound, the compound of formula (I-a) in which R'$_4$ is exchanged to an amino methyl group can be obtained by treating the compound of formula (VIII) with hydrogen gas atmosphere in the presence of Raney nickel under 40° C. and 50 psi in the same manner as in Step (g-1), and when R'$_4$ is an acetoxy compound, the compound of formula (1-b) in which R'$_4$ is exchanged to a hydroxy group can be obtained by treating with a weak base reagent such as potassium carbonate/methanol in the same manner as in Step (g-2).

The merits of the present invention are as follows:

First, the compound of formula (II) useful as a chiral building block can be produced from a low-priced optically active epoxide compound, and the various compounds of formula (I) can be produced therefrom;

Second, production costs can be reduced because expensive reagents and complicated devices for the reaction are necessary; and Third, the complex reaction steps are not included and thus, the synthesis reaction are simple.

EXAMPLES

Example 1

Preparation of (3R)-hydroxy-hex-5-en acid tert-butyl ester

Figure 1:
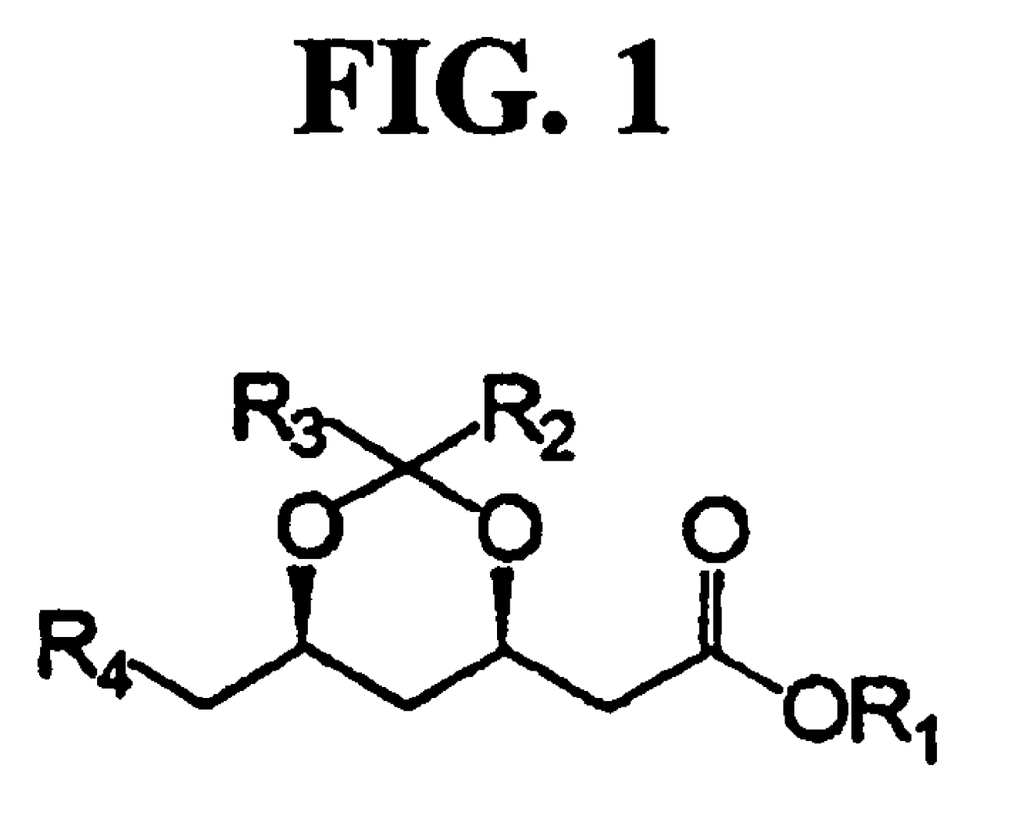
FIG. 1 is a drawing representing a chemical formula of a key chiral intermediate which is useful as a drug of hyperlipidemia The present invention is further defined by reference to the following examples described in detail, however these examples are not to be construed to limit the scope of the invention.

A round bottom flask was charged with 6.0 g (31.52 mmol) of CuI and add 500 ml of tetrahydrofurane. The mixture was cooled to −20° C., gradually added drop by drop 410 ml of vinyl magnesium bromide (1.0M in THF, 0.41 mol), and then agitated at the same temperature for 30 minutes.

Subsequently, the mixture was agitated for 1 hour together with being gradually adding drop by drop 50 g (0.3 g, 0.32 mol) of (S)-tert-butyl-3,4-epoxybutanoate (Choongwae Pharma Co,; *Science* 1997, 277, 936–938; JACS. 2000, 122, 1235–1236) diluted in 100 ml of tetrahydrofurane. The reaction solution obtained from mixture was added saturated ammonium chlorides to terminate the reaction. The solution was extracted with ethylacetate and the organic layer was washed with water and brine, and then dehydrated with anhydrous magnesium sulphate. The solvent was removed under decompressed pressure to give 52 g of (3R)-hydroxy-hex-5-en acid tert-butyl ester. The resulting compound was used to the subsequent reaction without a stage for another purification.

$^1$H NMR(300 MHz, CDCl$_3$) δ 1.47(s, 9H), 2.23–2.48(m, 4H), 3.08(1H, —OH), 4.0–4.07(m, 1H), 5.09(s, 1H), 5.14(d, J=4.18, 1H), 5.76–5.90(m, 1H).

$^{13}$C NMR(75 MHz, CDCl$_3$) δ 28.51, 41.28, 42.01, 67.90, 81.68, 118.35, 134.55, 172.70.

Example 2

Preparation of (3R)-tert-butoxycarbonyloxy-hex-5-en acid tert-butyl ester

A 1 liter, round bottom flask was charged with 52 g (0.29 mol) of (3R)-hydroxy-hex-5-en acid tert-butyl ester and the chemical was dissolved in 250 ml of tetrahydrofurane. The mixture was cooled to −20° C., gradually added drop by drop 116 ml (in 2.5M hexane, 0.29 mol) of n-butyl lithium and then was agitated for 30 minutes.

Subsequently, the reaction solution was gradually added drop by drop 63 g (0.29 mol) of di-tert-butyl dicarbonate dissolved in 100 ml of tetrahydrofurane, and then was agitated for 1 hour. To the solution of the reaction was then added water to terminate the reaction. The solution was extracted with ethylacetate, and the organic layer was washed with water and brine, and then dehydrated with anhydrous magnesium sulphate. The solvent was removed under decompressed pressure to obtain a crude compound. The resulting compound was subjected to the column chromatography (hexane:ethylacetate=50:1) to give 50.4 g of pure (3R)-tert-butoxycarbonyloxy-hex-5-en acid tert-butyl ester (Two stage yield: 56%).

$^1$H NMR(300 MHz, CDCl$_3$) δ 1.46(s, 9H), 1.49(s, 9H), 2.41(t, J=7.23, 2H), 2.48–2.61(m, 2H), 5.05–5.16(m, 3H), 5.73–5.87(m, 1H), $^{13}$C NMR(75 MHz, CDCl$_3$) δ 28.18, 38.93, 40.31, 73.19, 81.30, 82.37, 118.95, 133.20, 153.20, 169.80.

Example 3

Preparation of (4R-cis)-1,1-dimethylethyl-6-iodomethyl-2-oxo-1,3-dioxane-4-yl)-acetic acid tert-butyl ester A 500 ml, round bottom flask was charged with 10.0 g (34.92 mmol) of (3R)-tert-butoxycarbonyloxy-hex-5-en acid tert-butyl ester and then the chemical was dissolved in 100 ml of toluene. The mixture was cooled to −30° C., gradually added drop by drop 10.83 g (52.38 mmol) of iodomonobromide dissolved in 100 ml of trifluoromethylbenzene and then agitated the mixture at the same temperature for 30 minutes.

Next, the mixture was added saturated sodium thiosulphonate solution to terminate the reaction. The solution of the reaction was extracted with ethylacetate and the organic layer was washed with saturated sodium bicarbonate solution, water and brine, and then dehydrated with anhydrous magnesium sulphate. The solvent was removed under decompressed pressure to obtain a crude compound. The resulting compound was subjected to the column chromatography (hexane:ethylacetate=2:1) to give white solid of pure (4R-cis)-1,1-dimethylethyl-6-iodomethyl-2-oxo-1,3-dioxane-4-yl)-acetic acid 8.67 g (yield: 68%) and liquid of 390 mg of (4R-trans)-1,1-dimethylethyl-6-iodomethyl-2-oxo-1,3-dioxane-4-yl)-acetic acid tert-butyl ester.

Cis compound: $^1$H NMR(300 MHz, CDCl$_3$) δ 1.48(s, 9H), 1.73–1.85(m, 1H), 2.49–2.62(m, 2H), 2.77(dd, J=16.6, 6.08, 1H), 3.26–3.34(m, 1H), 3.41(dd, J=10.75, 4.48, 1H), 4.43–4.52(m, 1H), 4.81–4.90(m, 1H).

$^{13}$C NMR(75 MHz, CDCl$_3$) δ 5.987, 28.522, 33.351, 40.996, 75.20, 82.44, 148.84, 168.96.

Trans compound: $^1$H NMR(300 MHz, CDCl$_3$) δ 1.48(s, 9H), 2.17–2.28(m, 1H), 2.32–2.41(m, 1H), 2.57(dd, J=15.98, 7.77H), 2.81(dd, J=16.12, 6.44, 1H), 3.31(dd, J=10.5, 8.71, 1H), 3.47(dd, J=10.54, 4.52, 1H), 4.59–4.67 (m, 1H), 4.87–4.96(m, 1H).

Example 4

Preparation of (3R)-hydroxy-(4S)-oxyranyl-butyric acid tert-butyl ester

A 100 ml, round bottom flask was charged with 3.40 g (9.55 mmol) of (4R-cis)-1,1-dimethylethyl-6-iodomethyl-2-oxo-1,3-dioxane-4-yl)-acetic acid and then the compound was dissolved in 30 ml of anhydrous methanol. The mixture was added 4.0 g (28.94 mmol) of potassium carbonate and agitated at −30° C. for 1 hour, and then agitated at 0° C. for 4 hours.

After the completion of the reaction, the solution of the reaction was extracted with water and ethylacetate and then the organic layer was dehydrated with anhydrous magnesium sulphate. The solvent was removed under decompressed pressure to obtain a crude compound. The resulting compound was subjected to the column chromatography (hexane:ethylacetate=2:1) to give 1.54 g of (3R)-hydroxy-(4S)-oxyranyl-butyric acid tert-butyl ester (yield: 80%).

$^1$H NMR(300 MHz, CDCl$_3$) δ 1.47(s, 9H), 1.68–1.82(m, 2H), 2.47(d, J=6.84, 1H), 2.252(dd, J=4.96, 2.67, 1H), 2.79(t, J=4.93, 1H), 3.09–3.15(m, 1H), 3.386(d, J=3.4, 1H), 4.21(s, br, 1H).

$^{13}$C NMR(75 MHz, CDCl$_3$) δ 28.47, 39.23, 42.41, 46.95, 49.89, 66.60, 81.79, 172.46.

Example 5

Preparation of [(R-(R*,R*))-1,1-dimethylethyl 6-cyano-3,5-dihydroxy hexanate

A 250 ml, round bottom flask was charged with 1.15 g (5.70 mmol) of (3R)-hydroxy-(4S)-oxyranyl-butyric acid tert-butyl ester and then the chemical was dissolved in 40 ml of benzene. Subsequently, the reaction solution was added 3.23 g (11.38 mmol) of titanium isopropoxide. The mixture was agitated at room temperature for 30 minutes, was added 1.5 g (5.70 nmol) of 18-crown-6 and 3.70 g (5.70 mmol) of potassium cyanide and then the reaction solution agitated for 48 hours. To the reaction mixture was added a buffer solution (pH=7.0) to terminate the reaction. The solution of the reaction was extracted with ethylacetate, and the organic layer was washed with a saturated sodium carbonate solution, water and brine, and dehydrated with anhydrous magnesium sulphate. The solvent was removed under decompressed pressure to obtain a crude compound. The resulting compound was subjected to the column chromatography (hexane:ethylacetate=1:2) to give 1.01 g of [(R-(R*,R*))-1,1-dimethylethyl 6-cyano-3,5-dihydroxy hexanate (yield: 77%).

$^1$H NMR(300 MHz, CDCl$_3$) δ 1.47(s, 9H), 1.68–1.82(m, 2H), 2.47(d, J=6.84, 1H), 2.53(dd, J=4.96, 2.67, 1H), 2.78(t, J=4.93, 1H), 3.09–3.15(m, 1H), 3.39(1H), 4.21(m, 1H).

$^{13}$C NMR(75 MHz, CDCl$_3$) δ 26.24, 28.48, 41.21, 42.43, 69.02, 68.25, 82.49, 117.79, 172.49.

Example 6

Preparation of (4R-cis)-1,1-dimethylethyl 6-cyanomethyl2,2-dimethyl-1,3-dioxane-4-acetate A 100 ml, round bottom flask, was charged with 1.0 g (4.32 mmol) of 6-cyano-(3R,5S)-dihydroxyl-hexane acid tert-butyl ester and then the chemical was dissolved in 20 ml of acetone. Next, the reaction solution was added 110 mg (0.48 mmol) of camphorsulphonic acid and 0.54 g (5.18 mmol) of 2,2-dimethoxypropane. The mixture was agitated at room temperature for 1 hour.

After the completion of the reaction, acetone from solution was removed under depressed pressure. The mixture was added water, extracted with ethylacetate, and then organic layer was dehydrated with anhydrous magnesium sulphate. The resulting solution was subjected to the column chromatography (hexane:ethylacetate=4:1) to give 0.96 g of pure (4R-cis)-1,1-dimethylethyl 6-cyanomethyl 2,2-dimethyl-1,3-dioxane-4-acetate (yield: 83%).

$^1$H NMR(300 MHz, CDCl$_3$) δ 1.39(s, 3H), 1.46(d, J=4.05, 9H), 1.57(s, 4H), 1.76(dt, J=13.18, 2.26, 1H), 2.34(dd, J=15.47, 6.03, 1H), 2.43–2.53(m, 3H), 4.13–4.17(m, 1H), 4.24–4.33(m, 1H).

$^{13}$C NMR(75 MHz, CDCl$_3$) δ 19.99, 25.34, 28.48, 30.12, 35.79, 42.71, 66.06, 65.44, 81.27, 99.84, 117.16, 170.26.

Example 7

Preparation of (4R-cis)-1,1-dimethylethyl 6-(2-aminoethyl)-2,2-dimethyl-1,3-dioxane-4-acetate In a device of hydrogenation reaction, 0.96 g (3.56 mmol) of (4R-cis)-1,1-dimethylethyl 6-cyanomethyl 2,2-dimethyl-1,3-dioxane-4-acetate was dissolved in 15 ml of methanol saturated with anhydrous ammonium, 78 mg of the activated Raney nickel was added, and then the mixture was treated under hydrogen gas atmosphere at 40° C. under 50 psi.

When the reaction was completed after 20 hours, the mixed solution was cooled and filtrated. Then the solvent was concentrated under depressed pressure. Concentrated crude compound was subjected to the column chromatography (ethylacetate:methanol:ammonium hydroxide=30:20:1) to give 0.89 g of pure (4R-cis)-1,1-dimethylethyl 6-(2-aminoethyl)-2,2-dimethyl-1,3-dioxane-4-acetate (yield: 92%).

$^1$H NMR (300 MHz, CDCl$_3$) δ 1.0–1.2 (m, 1H), 1.22(s, 3H), 1.31 (s, 12H), 1.35–1.45(m, 3H), 2.15(dd, 1H, J=15.1 Hz, J=6.2 Hz), 2.29(dd, 1H, J=15.1 Hz, J=7.0 Hz), 2.66(t, 2H, J=6.6 Hz), 3.82(m, 1H), 4.12(m, 1H).

$^{13}$C NMR(75 MHz, CDCl$_3$) δ 19.60, 27.96, 30.00, 36.50, 38.25, 39.79, 42.61, 66.08, 67.18, 80.21, 98.35, 169.82.

Example 8

Preparation of [(R-(R*,R*))-1,1-dimethylethyl 6-acetoxymethyl-3,5-dihydroxy hexanate A 100 ml, round bottom flask was charged with 0.5 g (2.47 mmol) of (3R)-hydroxy-(4S)-oxyranyl-butyric acid tert-butyl ester and then the chemical was dissolved in 15 ml of benzene. Subsequently, the solution was added 0.63 ml (4.94 mmol) of trifluoroboron diethylether. The solution was agitated at room temperature for 30 minutes, and then was added 0.90 g of tetrabutylammonium iodide, and the resulting mixture was agitated for 24 hours.

Subsequently, the mixture was added a buffer solution (pH=7.0) to complete the reaction. The solution of the reaction was extracted with ethylacetate, and the organic layer was washed with saturated sodium carbonate solution, water and brine, and then dehydrated with anhydrous magnesium sulphate. The solvent was removed under decompressed pressure to obtain a crude compound. The resulting compound was subjected to the column chromatography (hexane:ethylacetate=1:1) to give 440 mg of [(R-(R*,R*))-1,1-dimethylethyl 6-acetoxymethyl-3,5-dihydroxy hexanate (yield: 68%).

$^1$H NMR (300 MHz, CDCl$_3$) δ 1.47(s, 9H), 1.61–1.70(m, 2H), 2.1(s, 3H), 2.42(d, J=6.5, 2H), 3.70(s, 1H, —OH), 3.85(s, 1H, —OH), 4.02–4.13(m, 3H), 4.22–4.31(m, 1H).

$^{13}$C NMR(75 MHz, CDCl$_3$) δ 21.28, 28.50, 38.94, 42.79, 68.57, 68.91, 70.23, 82.10, 171.53, 172.42

Example 9

Preparation of (4R-cis)-1,1-dimethylethyl 6-acetoxymethyl 2,2-dimethyl-1,3-dioxane-4-acetate A 100 ml, round bottom flask was charged with 0.25 g (0.95 mmol) of [(R-(R*,R*))-1,1-dimethylethyl 6-acetoxy-3,5-dihydroxy hexanate and then the chemical was dissolved in 10 ml of acetone. Subsequently, the solution was added 22 mg of camphorsulphonic acid and 0.12 g (1.14 mmol) of 2,2-dimethoxypropane. The mixture was agitated at room temperature for 6 hours.

After the completion of the reaction, acetone from the solution was removed under depressed pressure. The solution was added water, extracted with ethylacetate, and then the organic layer was dehydrated with anhydrous magnesium sulphate.

The resulting compound was subjected to the column chromatography (hexane:ethylacetate=10:1) to give 0.25 g of pure (4R-cis)-1,1-dimethylethyl 6-acetoxymethyl 2,2-dimethyl-1,3-dioxane-4-acetate (yield: 88%).

$^1$H NMR (300 MHz, CDCl$_3$) δ 1.39(s, 3H), 1.45(s, 9H), 1.47(s, 3H), 1.54–1.60(m, 2H), 2.08(s, 3H), 2.31(dd, J=15.2, 6.4, 1H), 2.46(dd, J=15.24, 6.72, 1H), 3.97–4.17(m, 3H), 4.34–4.24(m, 1H).

Example 10

Preparation of (4R-cis)-6-hydroxymethyl)-2,2-dimethyl-1,3-dioxane-4-acetic acid, 1,1-dimethylethyl ester 2 g (0.66 mmol) of (4R-cis)-1,1-dimethylethyl-6-acetoxymethyl-2,2-dimethyl-1,3-dioxane-4-acetate was dissolved in 5 ml of methanol. Subsequently, the solution was added 46 mg (0.33 mmol) of anhydrous potassium carbonate, agitated at room temperature for 30 minutes and then filtrated.

The solvent was removed under decompressed pressure. To the residue was added water and ethyl acetate, and extracted. The organic layer was washed with brine and then dehydrated with anhydrous magnesium sulphate. The solvent was removed under decompressed pressure and subjected to the column chromatography to give 156 mg of pure (4R-cis)-6-(hydroxymethyl)-2,2-dimethyl-1,3-dioxane-4-acetic acid, 1,1-dimethylethyl ester (yield: 92%).

$^1$H NMR (300 MHz, CDCl$_3$) δ 1.39(s, 3H), 1.44(s, 9H), 1.47(s, 3H), 1.51(t, J=2.51, 1H), 1.96(t, J=5.7, 1H), 2.31(dd, J=15.32, 6.03, 1H), 2.45(dd, J=15.31, 6.96, 1H), 3.46–3.53 (m, 1H), 3.58–3.65(m, 1H), 3.97–4.05(m, 1H), 4.25–4.34 (m, 1H).

What is claimed is:

1. A process for preparing the compound of formula (I) as shown in Scheme 2, characterized in that it comprises the following steps of:
   (a) reacting an epoxide compound of formula (III) with vinyl magnesium bromide or vinyl magnesium chloride to produce a β-hydroxy compound of formula (IV);
   (b) protecting the hydroxy group of β-hydroxy compound of formula (IV) with an alkyloxy carbonyl group by reacting the β-hydroxy compound of formula (IV) with dialkyldicarbonate such as di-tert-butyl dicarbonate to produce a compound of formula (V);
   (c) cyclization-reacting the compound of formula (V) by a iodolactone forming reacting to produce a compound of formula (VI);
   (d) treating the compound of formula (VI) with a weak base such as K$_2$CO$_3$, Na$_2$CO$_3$ to produce a compound of formula (II);
   (e) producing a 1,3-diol compound of formula (VII) by a ring opening reaction of the compound of formula (II) with various nucleophiles in the presence of a metal catalyst and a phase transition catalyst;
   (f) treating the 1,3-diol compound of formula (VII) with an acetylating agent or a ketalizing agent in the presence of an acid catalyst to transform the compound of formula (VII) into a compound of formula (VIII); and
   (g) if necessary, producing a compound of formula (I) by exchanging R'$_4$ group in the compound of formula (VIII):

[Scheme 2]

wherein R$_1$ denotes a hydrogen atom, alkyl, aryl or alkylaryl, R$_2$ and R$_3$ which can be identical or different, denote a lower alkyl or phenyl and are capable of forming a six-membered ring, R$_4$ stands for hydroxy, amino, alkylamino, arylamino, azido, cyano, halogeno, aryloxy, alkyloxy, arylalkyloxy, alkyl, alkenyl, aryl, or aminomethyl, etc. and R'$_4$ is the same as R$_4$ or a group of the precursor form.

2. A process for preparing the compound of formula (II) as the intermediate as shown in Scheme 2, characterized in that it comprises the following steps of:
(a) reacting an epoxide compound of formula (III) with vinyl magnesium bromide or vinyl magnesium chloride to produce a β-hydroxy compound of formula (IV);
(b) protecting the hydroxy group of β-hydroxy compound of formula (IV) with an alkyloxy carbonyl group by reacting the β-hydroxy compound of formula (IV) with dialkyldicarbonate such as di-tert-butyl dicarbonate to produce the compound of formula (V);
(c) cyclization-reacting the compound of formula (V) to produce a compound of formula (VI); and
(d) treating the compound of formula (VI) with a weak base such as $K_2CO_3$, $Na_2CO_3$ to produce a compound of formula (II).

3. The process as claimed in claim 1, wherein $R_4$ is —$CH_2NH_2$ or —OH, and $R'_4$ which is the precursor form of $R_4$ is —CN, —OAc or —OBn.

4. The process as claimed in claim 1, wherein $R_1$ is a methyl, ethyl, or tert-butyl group, and both $R_2$ and $R_3$ are methyl group.

5. The process as claimed in claim 1, wherein the reaction of Step (c) is carried out at temperature between −80° C. and 0° C. by IBr dissolved in either trifluoromethylbenzene itself or trifluoromethylbenzen together with an organic solvent such as toluene or benzene.

6. The process as claimed in claim 1, wherein the reaction of Step (d) is carried out under 3 equivalents of potassium carbonate/methanol or sodium carbonate/methanol at temperature between −78° C. and 0° C.

7. The process as claimed in claim 1, wherein the nucleophile used in Step (e) is MCN, MOAc or MOBn (wherein M denotes Li, Na, or K).

8. The process as claimed in claim 1, wherein the metal catalyst used in Step (e) is titanium isopropoxide[$Ti(O^iPr)_4$], aluminium isopropoxide[$Al(O^iPr)_3$] or trifluoroboron diethylether[$BF_3.OEt_2$], and the phase transition catalyst is 18-crown-6,15-crown-5,12-crown-4 or tetrabutylammonium halide.

9. The process as claimed in claim 2, wherein $R_1$ is a methyl, ethyl, or tert-butyl group, and both $R_2$ and $R_3$ are methyl group.

10. The process as claimed in claim 2, wherein the reaction of Step (c) is carried out at temperature between −80° C. and 0° C. by IBr dissolved in either trifluoromethylbenzene itself or trifluoromethylbenzen together with an organic solvent such as toluene or benzene.

11. The process as claimed in claim 2, wherein the reaction of Step (d) is carried out under 3 equivalents of potassium carbonate/methanol or sodium carbonate/methanol at temperature between −78° C. and 0° C.

* * * * *